United States Patent [19]

Siegel et al.

[11] Patent Number: 4,882,332
[45] Date of Patent: Nov. 21, 1989

[54] IMMUNE SUPPRESSION METHOD EMPLOYING ARLY-SUBSTITUTED NAPHTHYRIDINE AND PYRIDOPYRAZINE DERIVATIVES

[75] Inventors: Marvin I. Siegel, Woodbridge; Sidney R. Smith, Ridgewood, both of N.J.

[73] Assignee: Schering Corporation, Kenilworth, N.J.

[21] Appl. No.: 921,288

[22] Filed: Oct. 20, 1986

[51] Int. Cl.$^4$ .................... A61K 31/495; A61K 31/44
[52] U.S. Cl. ..................................... 514/255; 514/293
[58] Field of Search ................ 514/293, 255, 293, 255

[56] References Cited

U.S. PATENT DOCUMENTS 4,596,809  6/1986  Sherlock .
4,760,073  7/1988  Blythin et al. ...................... 514/293

FOREIGN PATENT DOCUMENTS 0127135 12/1984 European Pat. Off. .

OTHER PUBLICATIONS

Stites et al., Basic & Clinical Immunology, Lance Medical Publications, Los Altos, Calif. pp. 509–512 (1984).
Bulletin de la Societe Chimique de France, No. 1, 1968, pp. 364–369, C. Fournier, et al.
Derwent Abstract of Japanese Published Patent 58-144391 (8/83).

Primary Examiner—Jerome D. Goldberg
Attorney, Agent, or Firm—Joseph T. Majka; Gerald S. Rosen

[57] ABSTRACT

A method and composition for suppressing the immune response are disclosed which employ an immunosuppressing effective amount of certain aryl-substituted naphthyridines and pyrido-pyrazines.

13 Claims, No Drawings

IMMUNE SUPPRESSION METHOD EMPLOYING ARLY-SUBSTITUTED NAPHTHYRIDINE AND PYRIDOPYRAZINE DERIVATIVES

BACKGROUND OF THE INVENTION

This invention relates to the use of certain tricyclic naphthyridine and pyridopyrazine derivatives in suppressing the immune response in mammals.

SUMMARY OF THE INVENTION

The present invention involves a method for suppressing the immune response in a mammal which comprises administering to a mammal in need of such treatment in immunosuppressing effective amount of a compound having the structural formula I

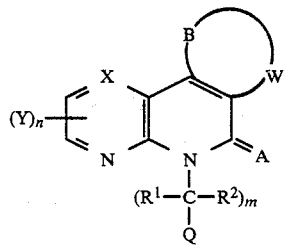

or a pharmaceutically acceptable salt or solvate thereof, wherein:

X represents CH or N;
A represents O or S;
m is an integer of from 0 to 2;
n is an integer of from 0 to 2;
$R^1$ and $R^2$ are the same or different and each is independently selected from H or alkyl;
W represents a covalent bond or a group selected from —O—, —S(O)$_p$—, —NH—, —N($R^4$)—, —N(COR$^4$)—, or —N(SO$_2$R$^4$)— {wherein p is an integer of from 0 to 2 and $R^4$ is alkyl};
B represents alkylene having from 2 to 8 carbon atoms, which alkylene may be optionally substituted with a group selected from —OH, —F, alkyl having from 1 to 4 carbon atoms, —CH$_2$OH, —CHO, —CO$_2$H, —COR$^3$ {wherein $R^3$ is selected from —NHR$^4$, —N(R$^4$)$_2$ or —OR$^4$ and $R^4$ is as defined above}, or —CN, with the proviso that OH or F is not on the carbon adjacent to W when W is —O—, —S(O)$_p$—, —NH—, —N(R$^4$), —N(COR$^4$)— or —N(SO$_2$R$^4$);
Q represents an aryl or an aromatic heterocyclic group which can optionally be substituted with up to 3 substituents Y as defined below; and
each Y substituent is independently selected from —OH, hydroxymethyl, alkyl, halo, —NO$_2$, alkoxy, —CF$_3$, —CN, cycloalkyl, alkynyloxy, alkenyloxy, —S(O)$_p$—R$^4$ {wherein R$^4$ and p are defined above}, —CO—R$^5$ {wherein R$^5$ represents —OH, —NH$_2$, —NHR$^4$, N(R$^4$)$_2$ or —OR$^4$ in which R$^4$ is as defined above}, —O—D—COR$^5$ {wherein D represents alkylene having from 1 to 4 carbon atoms and R$^5$ is as defined above}, —NH$_2$, —NHR$^4$, —N(R$^4$)$_2$ {wherein R$^4$ is as defined above} or —NHCOH. The compounds of formula I are the same compounds disclosed in U.S. application Ser. No. 851,068, filed Apr. 11, 1986.

Compounds of formula I in which W is oxygen or a covalent bond are preferred. Also, A is preferably oxygen, while X is preferably CH. The group —B—W— preferably represents an alkylene or alkyleneoxy group, preferably —(CH$_2$)$_4$—, —(CH$_2$)$_5$—, —(CH$_2$)$_3$O— or —(CH$_2$)$_4$O—. Other suitable —B—W— groups include —CH(OH)(CH$_2$)$_3$—, —CH$_2$CH(OH)(CH$_2$)$_2$—, —(CH$_2$)CH(OH)CH$_2$—, —(CH$_2$)$_3$CHOH—, —CH(CH$_2$OH)(CH$_2$)$_3$—, —CH$_2$CH(CH$_2$OH)CH$_2$—, —(CH$_2$)$_3$CH(CH$_2$OH)—, —CH(OH)(CH$_2$)$_4$—, —CH$_2$CH(OH)(CH$_2$)$_3$—, —(CH$_2$)$_2$—CH(OH)(CH$_2$)$_2$—, —(CH$_2$)$_2$CH(OH)CH$_2$—, —(CH$_2$)$_4$CH(OH)—, —CH(CH$_2$OH)(CH$_2$)$_4$—, —CH$_2$CH(CH$_2$OH)(CH$_2$)$_3$—, —(CH$_2$)$_2$CH(CH$_2$OH)(CH$_2$)$_2$—, —(CH$_2$)$_3$CH(CH$_2$OH)CH$_2$—, —(CH$_2$)$_4$CH(CH$_2$OH)—, —CH(OH)(CH$_2$)$_2$O—, —CH$_2$CH(OH)CH$_2$O—, —CH(CH$_2$OH)(CH$_2$)$_2$O—, —CH$_2$CH(CH$_2$OH)CH$_2$O—, —(CH$_2$)$_2$CH(CH$_2$OH)O—, —CH(OH)(CH$_2$)$_3$O—, —CH$_2$CH(OH)(CH$_2$)$_2$O—, —(CH$_2$)$_2$CH(OH)CH$_2$O—, —CH(CH$_2$OH)(CH$_2$)$_3$O—, —CH$_2$CH(CH$_2$OH)(CH$_2$)$_2$O—, —(CH$_2$)$_2$CH(CH$_2$OH)CH$_2$O—, and —(CH$_2$)$_3$CH(CH$_2$OH)O—. The letter n preferably represents zero and m is preferably zero. Q is preferably phenyl or Y-substituted phenyl, and in the latter case each Y substituent on the Q phenyl ring is preferably selected from chloro, nitro, methoxy or trifluoromethyl. The most preferred orientation for nitro, methoxy and trifluoromethyl substituents is in the meta position.

A preferred subgenus of compounds for use in the present invention is represented by the formula II

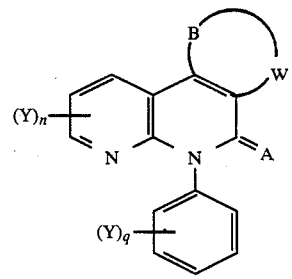

wherein A, B, W, n and Y are as defined above and q is 0 to 2.

When utilized herein, the terms below have the following scope:

halo-represents fluoro, chloro, bromo and iodo;

alkyl (including the alkyl portion of alkoxy) and alkylene—represent straight and branched carbon chains and, unless otherwise specified, contain from 1 to 6 carbon atoms;

alkenyloxy—represents straight and branched carbon atoms having at least one carbon to carbon double bond and, unless otherwise specified, contains from 3 to 6 carbon atoms, the alkenyl group thereof being bonded to an adjacent structural element through an oxygen atom;

alkynyloxy—represents straight and branched chains having at least one carbon to carbon triple bond and, unless otherwise specified, contains from 3 to 6 carbon atoms, the alkynyl group thereof being bonded to an adjacent structural element through an oxygen atom;

cycloalkyl—represents saturated carbocyclic rings having from 3 to 7 carbon atoms;

aryl—represents a carbocyclic group containing from 6 to 15 carbon atoms and having at least one benzene ring, with all available substitutable carbon atoms thereof being intended as possible points of attachment to the $(CR^1R^2)_m$ group or to the N atom if m is zero. More preferably, aryl is phenyl or Y-substituted phenyl. Suitable aryl groups include, e.g., phenyl, naphthyl, indenyl, indanyl, 3-chlorophenyl, 4-chlorophenyl, 4-fluorophenyl, etc.;

aromatic heterocyclic—represents cyclic groups having at least one O, S and/or N in the ring structure and having a sufficient number of delocalized pi electrons to provide aromatic character, with the aromatic heterocyclic groups preferably containing from 3 to 14 carbon atoms, e.g., 2-, 3- or 4-pyridyl, 2- or 3-furyl, 2- or 3-thienyl, 2-, 4- or 5-thiazolyl, 2-, 4- or 5-imidazolyl, 2- , 4-, 5- or 6-pyrimidinyl, 2- or 3-pyrazinyl, 3- or 4-pyradazinyl, 3-, 5- or 6-[1,2,4-triazinyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, etc., with all available substitutable carbon atoms thereof being intended as a possible point of attachment to the $(CR^1R^2)_m$ group or to the N atom if m is zero.

The invention also involves a pharmaceutical composition for suppressing the immune response which comprises an immunosuppressing effective amount of a compound of formula I above in combination with a pharmaceutically acceptable carrier.

DETAILED DESCRIPTION OF THE INVENTION

The compounds of formula I contain a $-(CR^1R^2)_m-$ substituent wherein each $R^1$ group and each $R^2$ group may vary independently. Thus, for example, when m equals 2 the following patterns of substitution (wherein hydrogen and $CH_3$ are used to represent any substituent, $R^1$ or $R^2$) are contemplated: $-C(CH_3)_2CH_2-$, $-CH_2C(CH_3)_2-$, $-CH_2CH(CH_3)-$, $-CH(CH_3)C-H_2-$, $-(C(CH_3)H)_2-$ and the like.

As noted above, the compounds of formula I may include one or two Y substituents on the fused ring system. Also, the Q group may include up to three Y substituents depending upon the available sites for substitution. In compounds where there is more than one such Y substituents, they may be the same or different. Thus, compounds having combinations of different Y substituents are contemplated within the scope of the invention. Examples of suitable Y substituents include hydroxy, methyl, chloro, bromo, methoxy, cyclohexyl, allyloxy, 2-propynyloxy, methylthio, methylsulfonyl, carboxy, acetoxy, N-methylaminocarbonyl, acetoxymethoxy, acetylamino, methylsulfonylamino and the like.

Compounds of formulas I and II can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of this invention.

Certain compounds of formula I may exist in isomeric forms. The invention contemplates all such isomers both in pure form and in admixture, including racemic mixtures.

Certain compounds of formula I also form pharmaceutically acceptable salts with organic and inorganic acids, e.g., the pyrido- or pyrazino-nitrogen atoms may form salts with strong acid while compounds having basic Y substituents such as amino groups also form salts with weaker acids. Examples of suitable acids for salt formation are hydrochloric, sulfuric, phosphoric, acetic, citric, oxalic, malonic, salicyclic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from the respective salt forms somewhat in certain physical properties, such as solubility in polar solvents, but the salts are otherwise equivalent to their respective free base forms for purposes of the invention.

Also, some compounds of formula I are acidic, e.g., when Y is OH, and can form salts with inorganic and organic bases.

The compounds of formula I may be synthesized from the corresponding 3-spiro-4-keto analogues of formula III below,

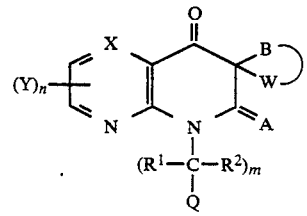

which may be synthesized following the procedures described in copending U.S. application Ser. Nos. 561,416, filed Dec. 14, 1983 and 641,076, filed Aug. 15, 1984 and in EPO Publication No. 0 144 996, published June 19, 1985, the disclosures of which are hereby incorporated by reference for this purpose. Alternative synthetic routes for the synthesis of these starting materials and substitutional variants thereof may be accomplished by those skilled in the art.

This process involves a selective reduction of the 4-keto group of the compound of formula III followed by dehydration and rearrangement in the presence of a strong organic or inorganic acid. In particular, compound of formula III is selectively reduced at the 4 position using a reducing agent capable of reducing ketones in the presence of an amide function in an acidic medium, e.g., a hydride reducing agent, to produce a compound of formula IV

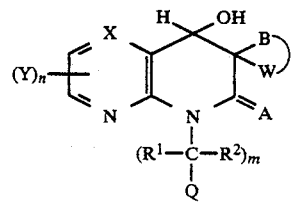

Examples of suitable reducing agents for this step are sodium cyanoborohydride and tert-butylamine borane. For a discussion of such selective reducing agents, see, for example, Herbert C. Brown, *Boranes in Organic Chemistry*, Cornell University Press, Ithaca and London, 1972, the relevant disclosure of which is hereby incorporated by reference. The reactions may be performed with cooling, with heating or at room temperature, as appropriate for the particular material being treated, e.g. at about 0° C. to about 40° C. Typically, the reaction is essentially complete in several minutes, but some reactions take several days to obtain maximum yield.

Suitable solvents are those which are capable of dissolving the starting materials and which do not react with the reducing agent to make the solution basic, of which aqueous alcohol and aqueous tetrahydrofuran in combination with a weak mineral or carboxylic acid, such as acetic acid, are examples.

The compounds according to structural formula IV are treated, either in their impure state or after suitable purification using techniques well known to those versed in the art, e.g., chromatography, with a strong organic or inorganic acid such as trifluoromethanesulfonic acid, H₂SO₄, methanesulfonic acid, Eaton's reagent, polyphosphoric acid, etc., or strongly acidic salts such as NaHSO₄. I have found that super acids having a Hammett acidity function of less than about minus 12, i.e., minus 13, minus 14, etc., provide particularly advantageous results in this process. Suitable super acids include trifluoromethanesulfonic acid, HF/BF₃, CH₃SO₃H/BF₃, etc. This measure of acidity is defined in Hammett, Louis P., and Deyup, Alden J., *Journal of the American Chemical Society*, Vol. 54, 1932, p. 2721. The time and temperature of the reaction can vary depending on the acid employed. For example, with CF₃SO₃H as the acid the temperature is generally in the range of from about room temperature (e.g., 25° C.) or below to about 150° C. Lower temperature (e.g., from about −78° C. to about 25° C.) may also be employed with for example, HF/BF₃. The acid is also generally used in excess, e.g., in an amount of from about 1.5 to about 30 equivalents. While not wishing to be bound to a specific mechanism, it appears that this treatment causes rearrangement of the spiro ring to form the ring

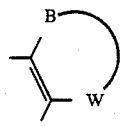

with the elimination of water, thus providing compounds of formula I. No diluent is required, but an inert cosolvent, such as halohydrocarbon, e.g., methylene chloride, may be used.

Certain compounds of formula I can be prepared by an alternative reaction scheme employing as starting materials compounds of the formula V

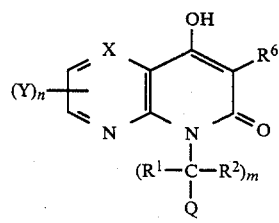

wherein R¹, R², Q, X, Y, m and n are as defined above and R⁶ is an alkyl group having from 2 to 8 carbon atoms. Such compounds can be prepared as described in U.S. Pat. No. 4,492,702 or by reaction of a compound of the formula VI with a compound of formula VII

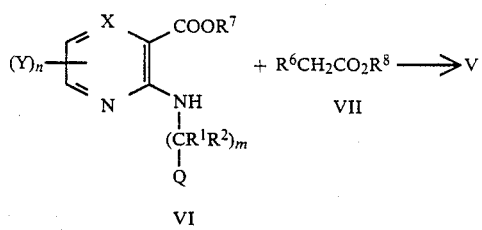

wherein R¹, R², R⁶, Q, X, Y, m and n are as defined above and R⁷ and R⁸ are the same or different and are alkyl of from 1 to 8 carbon atoms.

In this alternative method, the compound of formula V is first reacted with an electrophilic halogenating agent, e.g., Br₂, I₂+KI, ICl, etc., to produce a compound of formula VIII:

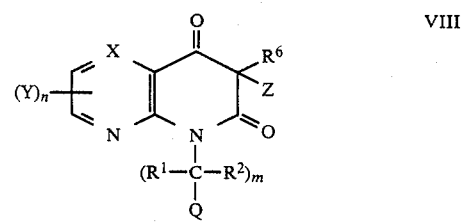

wherein Z represents halo. This reaction can be performed in an inert solvent and at any suitable temperature, preferably, at room temperature or below.

The compound of formula VIII is subjected to a nucleophilic displacement with an alcohol, e.g., an alkanol such as methanol or an arylkanol such as benzyl alcohol. For example, the compound of formula VIII may be reacted with 1,8-diazobicyclo[5.4.0]undec-7-ene [DBU] and an alcohol, with the alcohol group replacing the halide group to produce a compound of formula IX

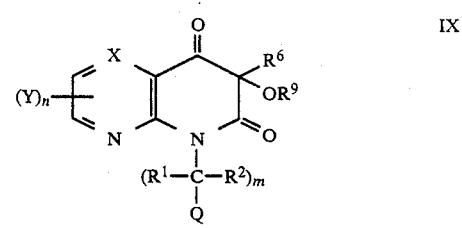

wherein R⁹ is the residue of the alcohol, e.g. alkyl group such as methyl or aralkyl group such as benzyl. This reaction may be conducted in an inert solvent and at any suitable temperature, again preferably at room temperature or below.

The compound of formula IX is reacted with a compound of the formula M—(CR¹⁰R¹¹)ᵣCR¹²=CR¹³R¹⁴ {wherein M is an alkali metal such as Li or is Mg-Z where Z is a halo group; R¹⁰, R¹¹, R¹², R¹³ and R¹⁴ may be the same or different and each is selected from H or alkyl having from 1 to 4 carbon atoms; and r is 0 or 1} to produce a compound of formula X

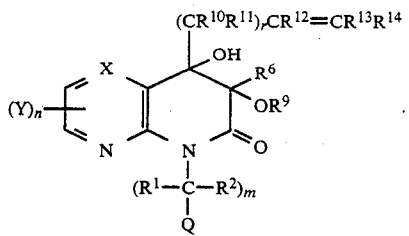

X

This reaction is performed under conventional conditions, e.g., in an inert solvent such as THF or diethyl ether and at any suitable temperature up to reflux.

The $R^9$ group is then removed with an ether cleaving reagent, e.g., $BBr_3$, $CF_3SO_3H$, $C_2H_5SH$ and $AlCl_3$, $K^+C_2H_5S^-$ in DMF, $Na^+C_2H_5S^-$ in DMF, etc., under conventional reaction conditions for such reactions to produce a compound of formula XI

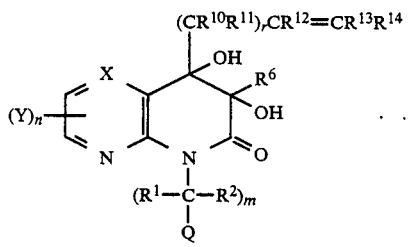

XI

The $R^6$ alkyl group is eliminated and a cyclization/dehydration is effected by use of a strong organic or inorganic acid, such as $CF_3SO_3H$, polyphosphoric acid, Eaton's reagent, $P_2O_5$ in $CHCl_3$, etc., to produce an alkene from the $R^6$ group and a compound of formula XII

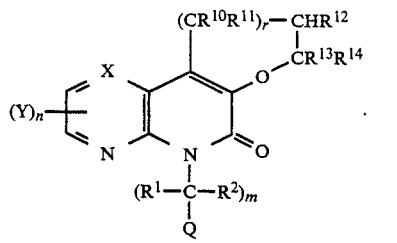

XII

When r is 1, the following isomer may also result:

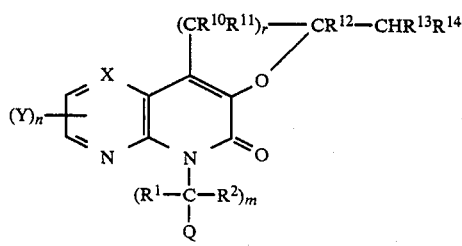

XIIa

This reaction can be performed neat or with an inert solvent and at any suitable temperature, preferably at room temperature or below.

In another method similar to that described in C. Keneko, T. Naito and M. Somei, *J.C.S. Chem. Comm.*, 804 (1979), a compound of formula XIII

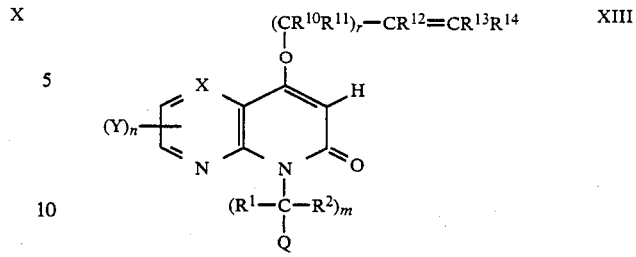

XIII

{wherein $R^1$, $R^2$, $R^{10}$, $R^{11}$, $R^{12}$, $R^{13}$, $R^{14}$, Q, X, Y, m, n and r are as defined above} can be irradiated with ultraviolet radiation, e.g., about 3000 Å, to produce a compound of formula XIV

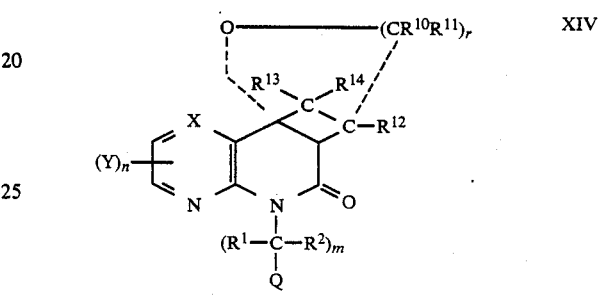

XIV

The compound of formula XIII is preferably in an inert solvent, e.g., an alcohol such as methanol or methanol/$CH_2Cl_2$, and the reaction mixture may be cooled during irradiation, if necessary. The starting compounds of formula XIII can be prepared by the methods described in U.S. Pat. No. 4,492,702.

The compound of formula XIV is reacted with a strong base such as a salt of an alcohol, e.g., a sodium or potassium alkoxide such as $NaOCH_3$, to produce a compound of formula XV

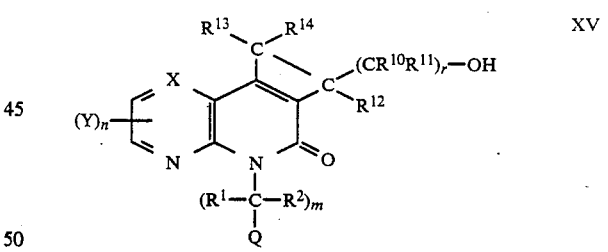

XV

This latter reaction can be conducted in an inert solvent, e.g., an alcohol such as methanol, and at any suitable temperature, preferably at about 75° to about 125° C.

The compounds of formula I wherein is sulfur may be obtained by treating the purified 2-carbonyl compound of formula I with thiating reagents well known in the art. Lawesson's Reagent {2,4-bis(4-methoxyphenyl-1,3-dithia-2,4-diphosphetane-2,4-disulfide} or one of its analogs, in toluene, or phosphorus pentasulfide in pyridine are suitable for this purpose.

The compounds of formula I are useful in the treatment of autoimmune and other immunological diseases including graft rejection in which T cell proliferation is a contributing factor to the pathogenesis of disease. The effectiveness of these compounds as immunosuppressing agents may be demonstrated by the following tests which involve the inhibition of T cell functions using these compounds.

GRAFT VS. HOST REACTION (GVHR)

To induce a GVHR, C57 B1/6XA/J(B6AF1) male mice were injected intravenously with parental (C57B1/6J) spleen and lymph node cells. The compound 1,2,3,4-tetrahydro-7-phenyl-oxepino[2,3-c][1,8]-naphthyridin-6(7H)-one (Compound A) was then administered orally for 10 days beginning on the day prior to the cell transfer. On the day following the last treatment, the animals were sacrificed, and their spleens were excised and weighed. The enlargement of the spleen of the host is a result of a GVHR. To some extent it is the host's own cells which infiltrate and enlarge the spleen although they do this because of the presence of graft cells reacting against the host. The amount of spleen enlargement, splenomegaly, is taken as a measure of the severity of the GVHR.

In carrying out the GVHR the animal in the experimental group is injected with parental cells, cells of the same species but of different genotype, which cause a weight increase of the spleen. The animal in the control group is injected with syngeneic cells, genetically identical cells which do not cause a weight increase of the spleen. The effectiveness of Compound A administered to the mice in the experimental group is measured by comparing the spleen weight of the untreated and treated GVH animal with that of the syngeneic control. Compound A reduced spleen weight by 61% as compared to the untreated animals at a dose of 10 mg/kg.

SPLENIC ATROPHY

The immunosuppressive activity of the compounds may also be shown by a decrease in spleen weight after dosing $BDF_1$ mice orally with the drug for seven (7) consecutive days. The mice are sacrificed on the eighth day. The percent decrease in spleen weight is measured for each dosage level. In this procedure (Compound A) provided a 30% spleen weight decrease at a dosage level of 100 mg/kg.

As mentioned in Ser. No. 851,068, filed Apr. 11, 1986, the subject compounds possess anti-allergy and anti-inflammatory activities. For example, Compound A has an $ED_{30}$ value of about 0.5 mg/kg p.o. in tests measuring the inhibition of anaphylactic bronchospasm in sensitized guinea pigs having antigen-induced bronchoconstriction and an $ED_{50}$ value of about 4.5 mg/kg p.o. in tests measuring the reverse passive Arthus reaction in the pleural cavity of rats (as described by Myers et al., *Inflammation*, Vol. 9, No. 1, 1985, pp. 91–98). Compound A has an $ED_{30}$ value of about 100 mg/kg in the splenic atrophy test as described above. These results for Compound A indicate that an immunosuppressive effective dose ($ED_{30}$) for such compounds is several times their anti-inflammatory and anti-allergy effective doses.

The usual dosage range for the compounds of formula I in a 70 kg mammal is an oral dose of about 0.1 to 250 mg/kg, preferably 0.1 to 150 mg/kg, in 3 or 4 divided doses per day. Of course, the dose will be regulated according to the potency of compound employed, the immunological disease being treated, and the judgment of the attending clinician depending on factors such as the degree and the severity of the disease state and age and general condition of the patient being treated.

To treat immunological diseases, the active compounds of formula I can be administered in unit dosage forms such as tablets, capsules, pills, powders, granules, sterile parenteral solutions or suspensions, suppositories, transdermal composition and the like. Such dosage forms are prepared according to standard techniques well known in the art.

For preparing pharmaceutical compositions from the compounds described by this invention, inert, pharmaceutically acceptable carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it may also be an encapsulating material. In powder, the carrier is a finely divided solid which is in admixture with the finely divided active compound. In the tablet, the active compound is mixed with carrier having the necessary binding properties in suitable proportions and compacted in the shape and size desired. The powders and tablets preferably contain from 5 to about 70% of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and other materials typically used in the pharmaceutical industries. The term "preparation" is intended to include the formulation of the active compound with encapsulating material as carrier, providing a capsule in which the active component (with or without other carriers) is surrounded by a carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution or suspension in aqueous polyethylene glycol solution. Aqueous solutions suitable for oral use can be prepared by adding the active component in water and adding suitable colorants, flavoring, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic aqueous salt solutions, ethanol, glycerine, proplyene glycol and the like, as well as mixtures thereof. The solvent utilized will be chosen with regard to the route of administration, for example, liquid preparations containing large amounts of ethanol are not generally suitable for parenteral use.

The compounds of the invention may also be deliverable transdermally for systemic distribution. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packaged tablets, capsules and powders in vials or ampules. The unit dosage form can also be a capsule, cachet or tablet itself, or it may be the appropriate number of any of these in a packaged form.

In the above modes of treatment, the dosage to be administered and the route of administration depends upon the particular compound selected, the age and general health of the subject, and the severity and type of condition to be controlled. Thus, the dose ultimately provided must be left to the judgment of a trained health-care practitioner.

The invention disclosed herein is exemplified by the following preparative examples, which should not be construed to limit the scope of the disclosure. Alternative mechanistic pathways and analogous structures within the scope of applicants invention, may be apparent to those skilled in the art.

PREPARATIVE EXAMPLE 1

1'-(3-Chlorophenyl)-1',4'-dihydro-4'-hydroxy-spiro[cyclopentane-1,3'(2'H)-[1,8]-naphthyridin]-2'-one To a solution of 2.2 g (6.73 mmol.) of 1'-(3-chlorophenyl)-spiro[cyclopentane-1,3'-[1,8]-naphthyridin]-2',4'-(1'H)dione in 176 mL of (1:1) THF: EtOH (abs.) was added 2.54 g (40 mmol.) of NaBH$_3$CN and 3.0 mL of acetic acid. The solution was stirred at room temperature. An additional 0.2 g (3.2 mmol.) of NaBH$_3$CN and 0.3 mL of acetic acid were added on the fourth day. After 9 days the reaction was stopped by slow addition of 10 mL of water. After concentration, the residue was purified by column chromatography, eluting with CHCl$_3$-CH$_3$OH(95:5) to yield a colorless solid, 1.82 g. (5.53 mmol. 82%).

Recrystallization from CHCl$_3$ and diethyl ether (Et$_2$O) yielded the product, m.p. 144°–146° C.

PREPARATIVE EXAMPLE 2

(SR,RS)-1-(3-Chlorophenyl)-4-hydroxy-1,3',4,4',5',6'-hexahydro-spiro[1,8-naphthyridine-3(2H),2'[2H]-pyran]-2-one (Compound A) and
(RS,RS)-1-(3-Chlorophenyl)-4-hydroxy-1,3',4,4',5',6'-hexahydro-spiro[1,8,-naphthyridine-3(2H),2'[2H]-pyran]-2-one (Compound B)

To a solution of 1.0 g (2.92 mmol.) of 1-(4-chloropheyl)-3',4',5',6'-tetrahydro-spiro[1,8-naphthyridine-3,2'-[2H]-pyran]-2,4-dione in 80 mL of (1:1) THF/C$_2$H$_5$OH (abs.) was added 0.734 g (11.66 mmol.) of NaBH$_3$CN and 0.6 mL of acetic acid. The solution was stirred at room temperature for 5 days, then it was quenched by the addition of 5 mL of water. After concentration, the residue was purified by column chromatography over silica gel, eluting with CHCl$_3$—CH$_3$OH (95:5), to yield 1.06 g (95%) of a mixture of the diastereomers, Compounds A and B. These were separated by preparative reversed-phase HPLC, eluting with CH$_3$CN—H$_2$O—CH$_3$COOH (30:70:1) to yield 0.52 g (54%) of Compound A, m.p. 183°–184.5° C., and 0.12 g (12%) of Compound B, m.p. 186.5°–188.5° C.

PREPARATIVE EXAMPLE 3

4-Hydroxy-1,3',4,4',5',6'-hexahydro-1-phenyl-spiro[1,8-naphthyridine-3(2H),2'[2H]-pyran]-2-one (mixture of diastereomers)

In a stirred mixture of tetrahydrofuran (THF) (200 mL) and C$_2$H$_5$OH (200 mL) was suspended 1-phenyl-3',4',5',6'-tetrahydro-spiro[1,8-naphthyridin-3,2'-[2H]-pyran]-2,4-dione (6.2 g) at room temperature. To the suspension was added acetic acid (2.6 mL) and tert-butylamine-borane (3.24 g).

After stirring for about 1 hour, water (ca. 200 mL) was added and the mixture was concentrated under vacuum to a volume of about 100 mL Additional water (400 mL) was added and the mixture was extracted with methylene chloride. The methylene chloride extract was separated, dried over sodium sulfate, filtered and concentrated. Ether was then added and the mixture was cooled. The resulting solid was removed by filtration, washed with fresh ether and dried to yield the desired product as a mixture of diastereomers, m.p. 211°–213° C.

By the methods described in Preparative Examples 1-3, the following compounds were prepared: 1',4'-Dihydro-4'-hydroxy-1'-phenyl-spiro[cyclopentane-1,3'-(2'H)[1,8]-naphthyridin]-2'-one,. m.p. 148°–150° C.; and 1',4'-dihydro-4'-hydroxy-1'-phenyl-spiro[furan-2,3-(2'H),[1,8]-naphthyridin]-2'-one, mixture of diastereomers, m.p. 220°–222° C.

EXAMPLE 1

7,8,9,10-Tetrahydro-5-phenyl-benzo[c][1,8]-naphthyridin-6-(5H)-one

A solution containing 1.2 g (4.07 mmol.) of 1',4'-dihydro-4'-hydroxy-1'-phenyl-spiro[cyclopentane-1,3'(2'H)-[1,8]-naphthyridin]-2'-one in 5.0 mL of trifluoromethanesulfonic acid was stirred at room temperature for 1.75 hours.

To this solution was added 100 mL of water and the resulting solution was adjusted to pH 5.0 with 2N NaOH. The precipitate was collected by filtration, washed with water, and redissolved in 200 mL of CH$_2$Cl$_2$. The organic solution was washed twice in 50 mL of saturated NaHCO₃ solution, then with 100 mL of H₂O, dried with MgSO₄, filtered, and concentrated in vacuo to yield 0.62 g (55%) of material, which was recrystallized from CHCl₃/Et₂O to yield the desired product, m.p. 160°–162° C.

EXAMPLE 2

2,3-Dihydro-6-phenyl-1H-pyrano[2,3,-c][1,8]-naphthyridin-5(6H)-one, ¼ H₂O

To trifluoromethanesulfonic acid (5.0 mL) was added slowly, in portions, 1′,4′-dihydro-4′-hydroxy-1′-phenylspiro[furan-2,3-(2′H)-[1,8]-naphthyridin]-2′-one (1.0 g) using a solid powder addition funnel, under N₂ at room temperature. The reaction was followed by HPLC and TLC which showed that one diastereomer rearranged faster than the other but that both eventually disappeared, after a total of about 24 hours.

The resulting solution was poured into ice-water (200 mL) containing NaOH (2.26 g). The pH was then adjusted to 4 with 1N HCl. The precipitate which formed on standing was collected, washed with water and purified by chromatography on silica gel (100 g), eluting with CH₂Cl₂ containing 2.5% of methanol, to yield the desired product, m.p. 250°–252° C.

In a similar manner, except for the length of time for which the reaction is run (progress followed by TLC), the following compounds were prepared:
5-(3-Chlorophenyl)-7,8,9,10-tetrahydro-benzo[c][1,8]-naphthyridin-6(5H)-one, m.p. 133°–135° C.;
7-Phenyl-1,2,3,4-tetrahydro-oxepino[2,3-c][1,8]-naphthyridin-6(7H)-one, m.p. 191°–193° C.; and
7-(3-Chlorophenyl)-1,2,3,4-tetrahydro-oxepino[2,3-c][1,8]-naphthyridin-6(7H)-one, m.p. 215°–217° C.

EXAMPLE 3

2,3-Dihydro-6-phenyl-1H-pyrano[2,3-c][1,8]-nanhythyridin-5(6H)-thione

A suspension of 2,3-dihydro-6-phenyl-1H-pyrano[2,3-c][1,8]-naphythyridin-5(6H)-one in dry toluene is stirred and heated in an N₂ atmosphere with a slight excess of Lawesson's Reagent [2,4-bis(4-methoxyphenyl)-1,3-dithia-2,4-diphosphetane-2,4-disulfide] at 50° C. then at gradually increasing temperatures (15° C. intervals, up to the reflux temperature) until TLC shows that reaction is occurring. Heating is continued until essentially no starting material remains; then the mixture is cooled, filtered, evaporated and purified by chromatography to yield the desired product.

By following the procedure of Example 3, or modifications well known to one skilled in the art, other sulfur-containing analogs of the invention may be produced.

EXAMPLE 4

1,2-Dihydro-5-phenylfuro[2,3-c][1,8]naphthyridin-4(5H)-one

Dissolve 3-n-butyl-4-hydroxy-1-phenyl-1,8-naphthyridin-2(1H)-one (10 g) in CH₂Cl₂ (1 L). Add a solution of Br₂ (1.74 mL, 5.43 g) in CH₂Cl₂ (30 mL) slowly. Stir briefly after the addition, then wash with water and evaporate. Recrystallize the intermediate bromo-compound (3-bromo-3-n-butyl-1-phenyl-1,8-naphthyridin-2,4(1H)-dione) from CH₂Cl₂/diethyl ether/hexane and redissolve it in CH₂Cl₂ (200 mL) and CH₃OH (75 mL). Add DBU (12 mL, about 3 equiv.) and stir at room temperature. Evaporate off the solvents after about 1 hour and redissolve the residue in CH₂Cl₂ (750 mL).

Add H₂O and adjust the aqueous layer to pH of about 4 with 1N HCl. Dry with MgSO₄ and evaporate. Recrystallize the product (3-n-butyl-3-methoxy-1-phenyl-1,8-naphthyridin-2,4(1H)-dione) from diethyl ether/CH₂Cl₂ and purify, if necessary, by chromatography over silica gel, eluting with CH₂Cl₂ containing 5% ethyl acetate.

Dissolve the purified product (5 g) in dry tetrahydrofuran (THF) (50 mL) and cool to below 0° C. Add a slight excess of vinyl magnesium bromide (1M in THF) and allow to react for 1 hour, then warm to room temperature. Add aqueous NH₄Cl solution (50 mL), evaporate off the THF and extract into CH₂Cl₂ (2×50 mL). Wash with H₂O (2×50 mL), dry with Na₂SO₄ and evaporate to yield a mixture of diastereomeric alcohols (diastereomers of 3-n-butyl-4-ethenyl-4-hydroxy-3-methoxy-1-phenyl-1,8-naphthyridin-2(1H)-one).

Dissolve the mixture in CH₂Cl₂ (50 mL) and cool to −78° C. Add a slight excess of BBr₃ in CH₂Cl₂ (10 mL) and stir for 1 hour. Allow to warm to room temperature, add H₂O (25 mL) and adjust the pH of the aqueous layer to 4. Separate the organic layer, wash with water (2×25 mL), dry with Na₂SO₄, and evaporate. Dissolve the crude product (3-n-butyl-4-ethenyl-3,4-dihydroxy-1-phenyl-1,8-naphthyridin-2(1H)-one) in cold CF₃SO₃H (below 0° C.) (20 mL) and stir until reaction is complete, as shown by HPLC analysis of a small sample. Allow to warm to room temperature, then pour into ice-water, adjust the pH to 4 and extract with CH₂Cl₂ (2×50 mL). Wash the organic layer with H₂O (2×25 mL), dry with MgSO₄, evaporate and purify by column chromatography over silica gel, eluting with increasing concentrations of ethyl acetate in CH₂Cl₂. Evaporate the fractions containing the product and recrystallize to yield the desired product.

EXAMPLE 5

1,2-Dihydro-2-(hydroxymethyl)-4-phenylcyclobuta(c)[1,8]naphthyridin-3(4H)-one

A solution of 4-(2-propenyloxy)-1-phenyl-1,8-naphthyridin-2(1H)-one (1.0 g) in methanol (350 mL) under an atmosphere of nitrogen was irradiated at 3000 Å for 3½ days. Solvent was removed under vacuum and the reaction product purified by chromatography on silica gel in CH₂Cl₂ containing 10% ethyl acetate. The fractions containing the product were combined and evaporated to yield 3(S R),9b(R S)-3,3a-dihydro-5-phenyl-3,9b-methano-2H-furo[3,2-c][1,8]naphthyridin-4(5H)-one, which was recrystallized from CH₂Cl₂/diethyl ether, m.p. 198°–199.5° C.

This compound (1.5 g) was dissolved in CH₃OH (100 mL). To the solution was added sodium methoxide (320 mg) and the mixture was heated at 90° C. under a nitrogen atmosphere for about 2.5 hours. Solvent was removed under vacuum, the residue suspended in water, and the pH adjusted to 4 with 1N HCl. The product was extracted with CH₂Cl₂ (3×100 mL) and the combined extracts washed with water (100 mL), dried with MgSO₄, and partially evaporated before separation on a silica gel chromatography column. The column was first eluted with CH₂Cl₂ containing 10% ethyl acetate, followed by CH₂Cl₂ containing 5% CH₃OH, and the product isolated from the relevant fractions, m.p. 204°–206° C.

By the methods of Examples 1–5 using suitably substituted reagents, the compounds according to Table III may be prepared.

TABLE III

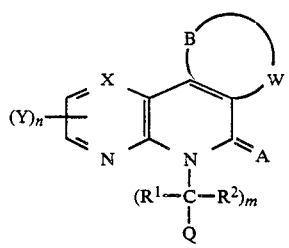

| X | n | Y* | m | R¹ | R² | A | B—W | Q |
|---|---|---|---|---|---|---|---|---|
| CH | 0 | — | 0 | — | — | O | $-CH_2CH_2CH_2O-$ | $C_6H_5-$ |
| CH | 0 | — | 0 | — | — | O | $-CH_2CH_2O-$ | $C_6H_5-$ |
| N | 0 | — | 0 | — | — | O | $-CH_2CH_2CH_2CH_2-$ | $C_6H_5-$ |
| N | 0 | — | 0 | — | — | O | $-CH_2CH_2CH_2CH_2-$ | $3-Cl-C_6H_4-$ |
| N | 0 | — | 0 | — | — | O | $-CH_2CH_2CH_2CH_2O-$ | $C_6H_5-$ |
| N | 0 | — | 0 | — | — | O | $-CH_2CH_2CH_2O-$ | $C_6H_5-$ |
| N | 0 | — | 0 | — | — | O | $-CH_2CH_2O-$ | $C_6H_5-$ |
| CH | 0 | — | 0 | — | — | S | $-CH_2CH_2CH_2CH_2O-$ | $C_6H_5-$ |
| CH | 0 | — | 0 | — | — | S | $-CH_2CH_2CH_2CH_2-$ | $C_6H_5-$ |
| CH | 1 | 7-$CH_3$ | 0 | — | — | O | $-CH_2CH_2CH_2O-$ | $4-CH_3O-C_6H_4-$ |
| CH | 0 | — | 0 | — | — | O | $-CH_2CH(OH)CH_2O-$ | $C_6H_5-$ |
| CH | 0 | — | 0 | — | — | O | $-CH_2CH(CH_2OH)CH_2-$ | $C_6H_5-$ |
| CH | 0 | — | 0 | — | — | O | $-CH_2CH_2CH(CH_2OH)O-$ | $C_6H_5-$ |
| CH | 0 | — | 0 | — | — | O | $-CH_2CH_2CH_2CH_2O-$ | $3-CH_3S-C_6H_4-$ |
| CH | 0 | — | 0 | — | — | O | $-CH_2CH_2CH_2CH_2-$ | $3-NO_2-C_6H_4-$ |
| CH | 0 | — | 0 | — | — | O | $-CH_2CH_2CH_2-$ | $3-Br-C_6H_4-$ |
| CH | 0 | — | 1 | H | H | O | $-CH_2CH_2CH_2N(CH_3)-$ | $3-CF_3-C_6H_4-$ |
| CH | 0 | — | 1 | $CH_3$ | H | O | $-CH_2CH_2CH_2-$ | (thienyl) |
| CH | 1 | 6-Cl | 1 | H | H | O | $-CH_2CH_2CH_2-S^+(O^-)-$ | $C_6H_5-$ |
| CH | 0 | — | 2 | H | H | O | $-CH_2CH_2CH_2O-$ | $4-F-C_6H_4-$ |
| CH | 0 | — | 1 | H | H | O | $-CH_2CH_2CH_2CH_2-$ | (naphthyl) |
| CH | 0 | — | 1 | H | H | O | $-CH_2CH_2CH_2O-$ | (pyridyl) |

*Numbering based on 1,8-naphthyridine.

The following formulations exemplify some of the dosage forms of the compositions of this invention. In each, the term "active compound" designates 1,2,3,4-tetrahydro-7-phenyl-oxepino[2,3-c][1,8]-naphthyridin-6(7H)-one. It is contemplated, however, that this compound may be replaced by equally effective amounts of other compounds of formula I.

PHARMACEUTICAL DOSAGE FORM EXAMPLES

EXAMPLE A

| | Tablets | | |
|---|---|---|---|
| No. | Ingredient | mg/tablet | mg/tablet |
| 1 | Active compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

METHOD OF MANUFACTURE

Mix Item Nos. 1 and 2 in a suitable mixer for 10-15 minutes. Granulate the mixture with Item No. 3. Mill the damp granules through a coarse screen (e.g., ¼") if needed. Dry the damp granules. Screen the dried granules if needed and mix with Item No. 4 and mix for 10-15 minutes. Add Item No. 5 and mix for 1-3 minutes. Compress the mixture to appropriate size and weight on a suitable tablet machine.

EXAMPLE B

| | Capsules | | |
|---|---|---|---|
| No. | Ingredient | mg/capsule | mg/capsule |
| 1 | Active compound | 100 | 500 |

| | Capsules | | |
|---|---|---|---|
| No. | Ingredient | mg/capsule | mg/capsule |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

METHOD OF MANUFACTURE

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

EXAMPLE C

| | Parenteral | |
|---|---|---|
| Ingredient | mg/vial | mg/vial |
| Active Compound Sterile Powder | 100 | 500 |

Add sterile water for injection or bacteriostatic water for injection, for reconstitution.

EXAMPLE D

| | Injectable |
|---|---|
| Ingredient | mg/vial |
| Active Compound | 100 |
| Methyl p-hydroxybenzoate | 1.8 |
| Propyl p-hydroxybenzoate | 0.2 |
| Sodium Bisulfite | 3.2 |
| Disodium Edetate | 0.1 |
| Sodium Sulfate | 2.6 |
| Water for Injection q.s. ad | 1.0 ml |

METHOD OF MANUFACTURE (for 1000 vials)

1. Dissolve p-hydroxybenzoate compounds in a portion (85% of the final volume) of the water for injection at 65°-70° C.
2. Cool to 25°-35° C. Charge and dissolve the sodium bisulfite, disodium edetate and sodium sulfate.
3. Charge and dissolve active compound.
4. Bring the solution to final volume by added water for injection.
5. Filter the solution through 0.22 membrane and fill into appropriate containers.
6. Finally sterilize the units by autoclaving.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method for suppressing T cell functions of the immune response in a mammal which comprises administering to a mammal in need of such treatment an immunosuppressing effective amount of a compound having the structural formula I

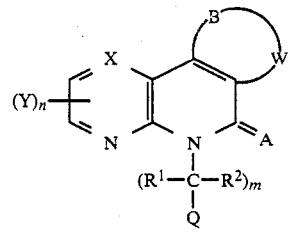

or a pharmaceutically acceptable salt or solvate thereof, wherein:

X represents CH or N;
A represents O or S,
m is an integer of from 0 to 2;
n is an integer of from 0 to 2;
$R^1$ and $R^2$ are the same or different and each is independently selected from H or alkyl containing 1 to 6 carbon atoms;
W represents —O— or —S(O)$_p$—, wherein p is an integer of from 0 to 2;
B represents alkylene having from 2 to 8 carbon atoms, which alkylene may be optionally substituted with a group selected from —OH, —F, alkyl having 1 to 4 carbon atoms, —CH$_2$OH, —CHO, —CO$_2$H, —COR$^3$ wherein R$^3$ is selected from —NHR$^4$, —N(R$^4$)$_2$ or —OR$^4$ wherein R$^4$ is alkyl of 1 to 6 carbon atoms or —CN, with the proviso that OH or F is not on the carbon atom adjacent to W;
Q represents an aryl group containing from 6 to 15 carbon atoms or an aromatic heterocyclic group containing from 3 to 14 carbon atoms and having at least one O, S or N in the ring, which aryl or aromatic heterocyclic group can optionally be substituted with up to 3 substituents Y as defined below; and
each Y substituent is independently selected from —OH, hydroxymethyl, alkyl containing from 1 to 6 carbon atoms, halo, —NO$_2$, alkoxy containing 1 to 6 carbon atoms, —CF$_3$, —CN, cycloalkyl containing 3 to 7 carbon atoms, alkenyloxy containing from 3 to 6 carbon atoms, alkynyloxy containing from 3 to 6 carbon atoms, —S(O)$_p$—R$^4$ wherein R$^4$ and p are as defind above, —CO—R$^5$ wherein R$^5$ represents —OH, —NH$_2$, —NHR$^4$, —N(R$^4$)$_2$ or —OR$^4$ in which R$^4$ is as defined above, —O—D—COR$^5$ wherein D represents alkylene having from 1 to 4 carbon atoms and R$^5$ is as defined above, —NH$_2$, —NHR$^4$, —N(R$^4$)$_2$ wherein R$^4$ is as defined above or —NHCOH.

2. A method according to claim 1 wherein W in formula I is oxygen.
3. A method according to claim 2 wherein A in formula I is oxygen.
4. A method according to claim 3 wherein X in formula I represents CH.
5. A method according to claim 4 wherein —B—W— in formula I represents an alkyleneoxy group of which may be substituted as defined in claim 1.
6. A method according to claim 5 wherein —B—W— in formula I represents —(CH$_2$)$_4$—O— or —(CH$_2$)$_3$—O—.
7. A method according to claim 5 wherein m in formula I equals zero.
8. A method according to claim 7 wherein n in formula I equals zero.

9. A method according to claim 8 wherein Q in formula I represents phenyl or substituted phenyl.

10. A method according to claim 9 wherein the one to three Y substituents on the Q phenyl group are each independently selected from chloro, nitro or trifluoromethyl.

11. A method according to claim 1 wherein the compound administered has the formula II

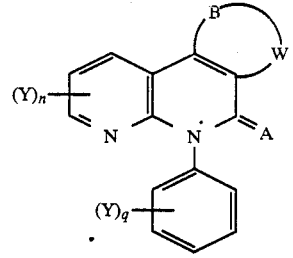

wherein A, B, W, Y and n are as defined in claim 1 and q is 0 to 2, and wherein, if n+q is greater than 1, the Y groups may be the same or different.

12. A method according to claim 1 wherein the compound administered is selected from
7-phenyl-1,2,3,4-tetrahydro-oxepino[2,3-c]-[1,8]-naphthyridin-6(7H)-one.
2,3-dihydro-6-phenyl-1H-pyrano[2,3-c][1,8]-naphthyridin-5(6H)-one; or
1,2-dihydro-5-phenylfuro[2,3-c][1,8]-naphthyridin-4-one; or
1,2-dihydro-2-(hydroxymethyl)-4-phenylcyclobuta(c)[1,8]naphthyridin-3(4H)-one.

13. A method according to claim 1 wherein the compound administered comprises 7-(3-chlorophenyl)-1,2,3,4-tetrahydro-oxepino[2,3-c][1,8]-naphthyridin-6(7H)-one.

* * * * *